(12) United States Patent
Huang et al.

(10) Patent No.: US 12,171,534 B2
(45) Date of Patent: *Dec. 24, 2024

(54) 3D PHYSIOLOGICAL DETECTION SYSTEM AND HOST DISPLAYING 3D ENERGY DISTRIBUTION

(71) Applicant: PixArt Imaging Inc., Hsin-Chu County (TW)

(72) Inventors: Sen-Huang Huang, Hsin-Chu County (TW); Ren-Hau Gu, Hsin-Chu County (TW)

(73) Assignee: PIXART IMAGING INC., Hsin-Chu County (TW)

(*) Notice: Subject to any disclaimer, the term of this patent is extended or adjusted under 35 U.S.C. 154(b) by 849 days.

This patent is subject to a terminal disclaimer.

(21) Appl. No.: 17/362,297

(22) Filed: Jun. 29, 2021

(65) Prior Publication Data
US 2021/0321891 A1 Oct. 21, 2021

Related U.S. Application Data

(60) Continuation of application No. 16/412,702, filed on May 15, 2019, now Pat. No. 11,076,768, which is a
(Continued)

(30) Foreign Application Priority Data
Dec. 23, 2014 (TW) ................... 103145066

(51) Int. Cl.
*A61B 5/024* (2006.01)
*A61B 5/00* (2006.01)

(52) U.S. Cl.
CPC ........ *A61B 5/02427* (2013.01); *A61B 5/7257* (2013.01); *A61B 2562/0238* (2013.01); *A61B 2562/04* (2013.01); *A61B 2576/00* (2013.01)

(58) Field of Classification Search
CPC ............. A61B 5/02427; A61B 5/7257; A61B 2562/0238; A61B 2562/04; A61B 2576/00
See application file for complete search history.

(56) References Cited

U.S. PATENT DOCUMENTS 5,797,840 A * 8/1998 Akselrod ............. A61B 5/4035
600/300
8,761,855 B2 * 6/2014 Watson ............. A61B 5/14551
600/323

(Continued)

FOREIGN PATENT DOCUMENTS

EP 2438849 A1 * 4/2012 ......... A61B 5/02416
WO WO-2011026986 A1 * 3/2011 ......... A61B 5/02416

*Primary Examiner* — Lindsey G Wehrheim
(74) *Attorney, Agent, or Firm* — WPAT, P.C

(57) ABSTRACT

A physiological detection system including an image sensor, a converting unit, a retrieving unit and a processing unit is provided. The image sensor includes a plurality of pixels respectively configured to output a PPG signal. The converting unit is configured to convert a plurality of PPG signals of a plurality of pixels regions to a plurality of frequency domain signals. The retrieving unit is configured to respectively retrieve a spectral energy of the frequency domain signals corresponding to each of the pixel regions. The processing unit is configured to construct a 3D energy distribution according to the spectral energies.

20 Claims, 5 Drawing Sheets

Related U.S. Application Data division of application No. 14/847,143, filed on Sep. 8, 2015, now Pat. No. 10,335,046.

(56) References Cited

U.S. PATENT DOCUMENTS

| | | | |
|---|---|---|---|
| 10,335,046 B2* | 7/2019 | Huang | A61B 5/02427 |
| 2005/0070774 A1* | 3/2005 | Addison | A61B 5/726 |
| | | | 600/323 |
| 2008/0045818 A1* | 2/2008 | Wood | A61B 5/15003 |
| | | | 600/573 |
| 2010/0113948 A1* | 5/2010 | Yang | A61B 5/02416 |
| | | | 600/500 |

\* cited by examiner

3D PHYSIOLOGICAL DETECTION SYSTEM AND HOST DISPLAYING 3D ENERGY DISTRIBUTION

CROSS REFERENCE TO RELATED APPLICATION

This application is a continuation application of U.S. application Ser. No. 16/412,702, filed on May 15, 2019, which is a divisional application of U.S. application Ser. No. 14/847,143, filed on Sep. 8, 2015, which claims the priority benefit of Taiwan Patent Application Serial Number 103145066, filed on Dec. 23, 2014, the full disclosure of which is incorporated herein by reference.

BACKGROUND

1. Field of the Disclosure

This disclosure generally relates to a physiological detection system and, more particularly, to a physiological detection system capable of detecting physiological characteristics of at least three dimensions and an operating method thereof.

2. Description of the Related Art

Nowadays, the portable electronic device and the wearable electronic device are indispensable electronic products in everyday life, and functions thereof are continuously progressed with the change of lifestyle.

Meanwhile, body health is concerned by people in the busy modern life. Accordingly, the physiologically detection function is gradually applied to portable electronic devices and wearable electronic devices to fulfill the requirements of users.

SUMMARY

Accordingly, the present disclosure provides a physiological detection system and an operating method thereof capable of detecting and recording at least three dimensional physiological characteristics of the user.

The present disclosure provides a physiological detection system and an operating method thereof that detect the physiological characteristics of different body tissues being detected through a plurality of pixel regions so as to generate a three dimensional physiological characteristic distribution.

The present disclosure further provides a physiological detection system and an operating method thereof capable of long-term recording the physiological characteristic variation of a three dimensional physiological characteristic distribution of different body tissues being detected so as to realize the function of long-term monitoring.

The present disclosure further provides a host configured to receive a plurality of PPG signals each corresponding to one pixel region of a frame acquired by a wearable device. The host includes a converting unit, a retrieving unit, a processing unit and a display. The converting unit is configured to convert each of the PPG signals to a frequency domain signal thereby generating a plurality of frequency domain signals each corresponding to one of pixel regions. The retrieving unit is configured to respectively retrieve a spectral energy value of the frequency domain signals corresponding to each of the pixel regions. The processing unit is configured to construct a three dimensional energy distribution of spectral energy values, each spectral energy value corresponding to one of the pixel regions, by distributing the spectral energy values in a two dimensional space corresponding to the pixel regions as the three dimensional energy distribution that has an energy value corresponding to each of the pixel regions. The display is configured to display the three dimensional energy distribution.

The present disclosure further provides physiological detection system includes a wearable device and a host. The wearable device is configured to output a plurality of PPG signals each corresponding to one pixel region of a frame acquired thereby. The host is configured to receive the plurality of PPG signals from the wearable device and includes converting unit, a retrieving unit, a processing unit and a display. The converting unit is configured to convert each of the PPG signals to a frequency domain signal thereby generating a plurality of frequency domain signals each corresponding to one of pixel regions. The retrieving unit is configured to respectively retrieve a spectral energy value of the frequency domain signals corresponding to each of the pixel regions. The processing unit is configured to construct a three dimensional energy distribution of spectral energy values, each spectral energy value corresponding to one of the pixel regions, by distributing the spectral energy values in a two dimensional space corresponding to the pixel regions as the three dimensional energy distribution that has an energy value corresponding to each of the pixel regions. The display is configured to display the three dimensional energy distribution.

In the physiological detection system and the operating method of the present disclosure, a three dimensional energy variation of the three dimensional energy distribution with time is further constructed so as to form a four dimensional physiological detection system.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
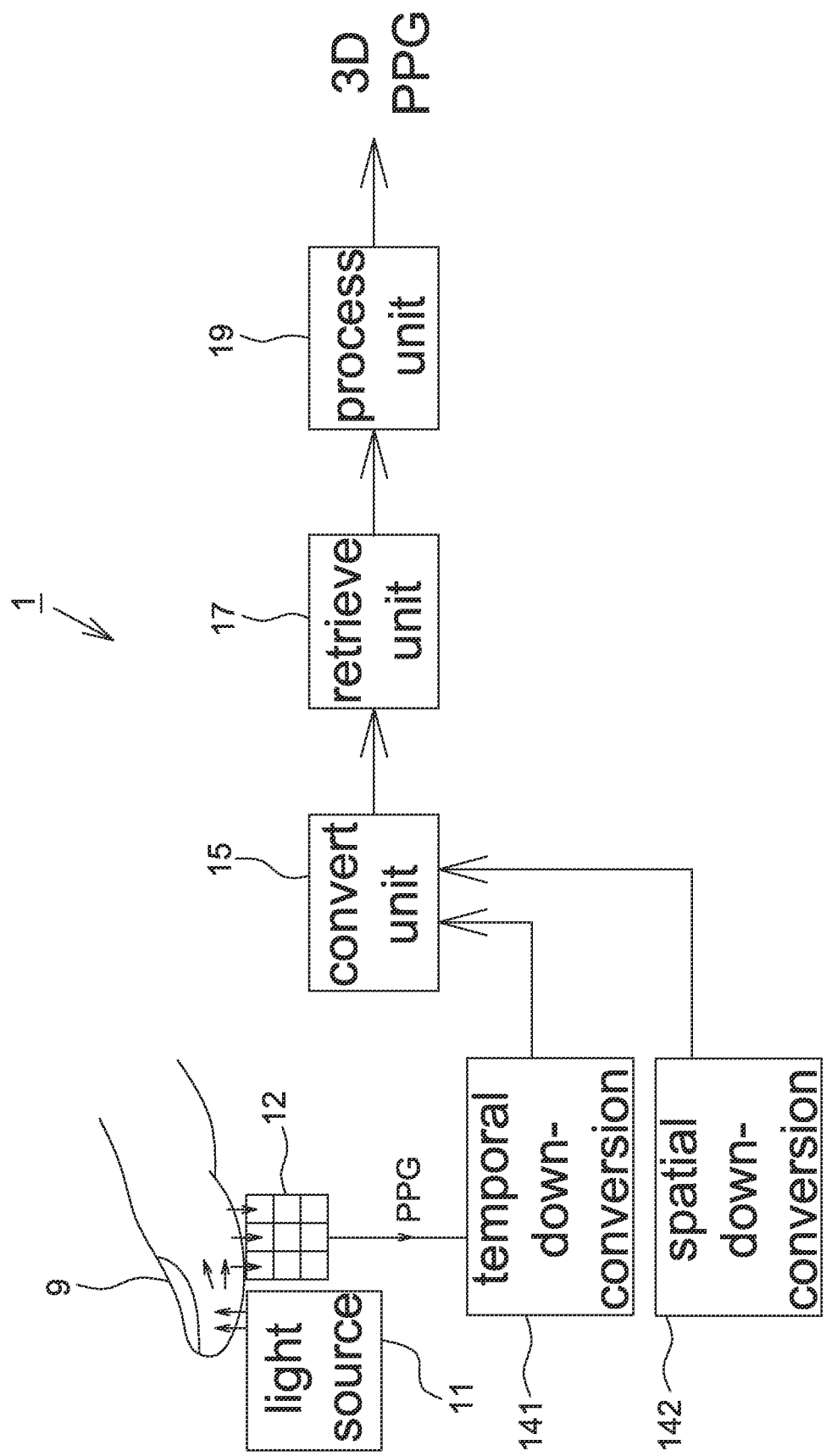
FIG. 1 is a schematic block diagram of a physiological detection system according to one embodiment of the present disclosure.

Referring to FIG. 1, it is a schematic block diagram of a physiological detection system according to one embodiment of the present disclosure. The physiological detection system 1 detects a three dimensional energy distribution of photoplethysmographic (PPG) signals of body tissues through a skin surface (e.g. taking a finger 9 as an example herein, but not limited to), wherein the three dimensional energy distribution is used to analyze tissue information of the human body being detected, e.g. microcirculation information, so as to help the user to monitor his/her own health. In addition, the physiological detection system 1 of the present disclosure is applicable to the portable electronic device or the wearable electronic device to realize a portable physiological detection device, and is suitable to the long-term self-monitoring. For example, it is able to monitor a three dimensional energy variation with time of the three dimensional energy distribution for a long time, e.g. monitoring a variation of the microcirculation information with time. Accordingly, it is able to obtain reliable physiological state information according to the obtained monitoring data in conjunction with the short-term testing results made in the medical facility.

In one embodiment, the physiological detection system 1 includes a light source 11, an image sensor (e.g. taking a sensor array as an example herein) 12, a converting unit 15, a retrieving unit 17 and a processing unit 19. In some embodiments, the physiological detection system 1 further includes a temporal down-conversion unit 141 and a spatial down-conversion unit 142 (illustrated by examples hereinafter) so as to reduce the data amount to be processed. In some embodiments, the retrieving unit 17 is included in the processing unit 19. For example, the retrieving unit 17 is a program executed by or an integrated circuit integrated in the processing unit 19 without particular limitations.

When the physiological detection system 1 is applied to a portable electronic device or a wearable electronic device, for saving power of the device, the light source 11, the image sensor 12, the temporal down-conversion unit 141 and the spatial down-conversion unit 142 are disposed in an image sensor chip; whereas the converting unit 15, the retrieving unit 17 and the processing unit 19 are disposed in a host external to the physiological detection device, wherein the physiological detection device includes the image sensor chip and communicates with the host wired or wirelessly. For example, the temporal down-conversion unit 141 and the spatial down-conversion unit 142 are included in a digital signal processor (DSP) of the image sensor chip, and implemented by software and/or hardware; whereas the converting unit 15, the retrieving unit 17 and the processing unit 19 are included in a microprocessor (MCU) or a central processing unit (CPU) of the host, and implemented by software and/or hardware. However, according to different applications, all elements of the physiological detection system 1 are disposed in an image sensor chip without particular limitations. For example, the temporal down-conversion unit 141, the spatial down-conversion unit 142, the converting unit 15, the retrieving unit 17 and the processing unit 19 are included in a digital signal processor (DSP) of the image sensor chip, and implemented by software and/or hardware.

The light source 11 is configured to illuminate a skin surface, and the light emitted from the light source 11 penetrates body tissues and then is received by the image sensor 12. For example, FIG. 1 shows that the light source 11 is configured to illuminate the skin surface of a finger 9. After the light emitted by the light source 11 passes through internal tissues of the finger 9, the penetrating light is received by the image sensor 12. The light emitted by the light source 11 is suitable to be absorbed by the body tissues, e.g. a red light beam (e.g. wavelength of about 660 nm) or an infrared light beam (e.g. wavelength of about 910 nm). As the oxyhemoglobin and the deoxyhemoglobin have different absorptivity at specific light spectrums, the light passing through the body tissues has an amplitude variation with heartbeats. The electrical signal outputted by the image sensor 12 for sensing the light with the amplitude variation is referred to a photoplethysmographic (PPG) signal herein, wherein waveforms of the PPG signal are known to the art and thus details thereof are not described herein.

It should be mentioned that although FIG. 1 shows a reflective physiological detection system (i.e. the light source 11 and the image sensor 12 at a same side of a skin surface), but the present disclosure is not limited thereto. The physiological detection system 1 of the present disclosure is also applicable to a transmissive physiological detection system (i.e. the light source 11 and the image sensor 12 at different sides of a skin surface) without particular limitations.

The image sensor 12 is preferably an active image sensor, e.g. including a CMOS image sensor, which has a sensor array including a plurality of pixels. The pixels are configured to detect light passing through body tissues and with the amplitude variation, and respectively output a PPG signal. In some embodiments, a sensor array of the image sensor 12 is divided into a plurality of pixel regions and each of the pixel regions includes a plurality of pixels. The image sensor 12 is able to add the PPG signals outputted by the pixels of each of the pixel regions to respectively output a sum of PPG signals thereby increasing the signal strength and reducing the data amount to be calculated. For example, the image sensor 12 includes a sensor array having 320×256 pixels, and every 8×8 pixels of the image sensor 12 is divided as a pixel region such that the sensor array is divided into 40×32 pixel regions.

In some embodiments, the image sensor 12 calculates a sum of analog PPG signals or a sum of digital PPG signals to be served as the sum of PPG signals. For example, the image sensor 12 further includes an analog-to-digital converter (ADC) configured to convert analog signals to digital signals. In one embodiment, the image sensor 12 adds the PPG signals outputted by the pixels in each of the pixel regions by the electric circuit previous to the ADC converter so as to generate a plurality of sum of PPG signals, and then the ADC converter converts the sum of PPG signals to digital signals. In another embodiment, the ADC converter firstly converts the analog PPG signal outputted by each pixel of the image sensor 12 to a digital PPG signal, and then the digital PPG signals are summed by software so as to generate a plurality of sum of PPG signals.

However, in other embodiments, the image sensor 12 outputs the PPG signal of each pixel without dividing the sensor array and calculating said sum of PPG signals.

The converting unit 15 converts a plurality of PPG signals of a plurality of pixel regions to a plurality of frequency domain signals (illustrated by examples hereinafter). In this embodiment, when a plurality of pixels in the image sensor 12 is not divided as a pixel region, each pixel region is referred to a single pixel; whereas when a plurality of pixels in the image sensor 12 is divided as a pixel region, each pixel region includes a plurality of pixels. In other words, in the present disclosure, the pixel region includes at least one pixel.

The retrieving unit 17 is configured to respectively retrieve a spectral energy value (illustrated by examples hereinafter) of the frequency domain signals corresponding to each of the pixel regions to be provided to the processing unit 19. The processing unit 19 then constructs a three dimensional energy distribution according to the spectral energy values, wherein the three dimensional energy distribution has an energy value corresponding to each of the pixel regions. In some embodiments, the processing unit 19 further interpolates the energy values received from the retrieving unit 17 so as to increase a resolution of the three dimensional energy distribution. In addition, the physiological detection system 1 further includes a memory (not shown). The processing unit 19 further constructs a three dimensional energy variation with time of the three dimensional energy distribution, which is stored in the memory, to be served as a four dimensional physiological information.

Figure 2:
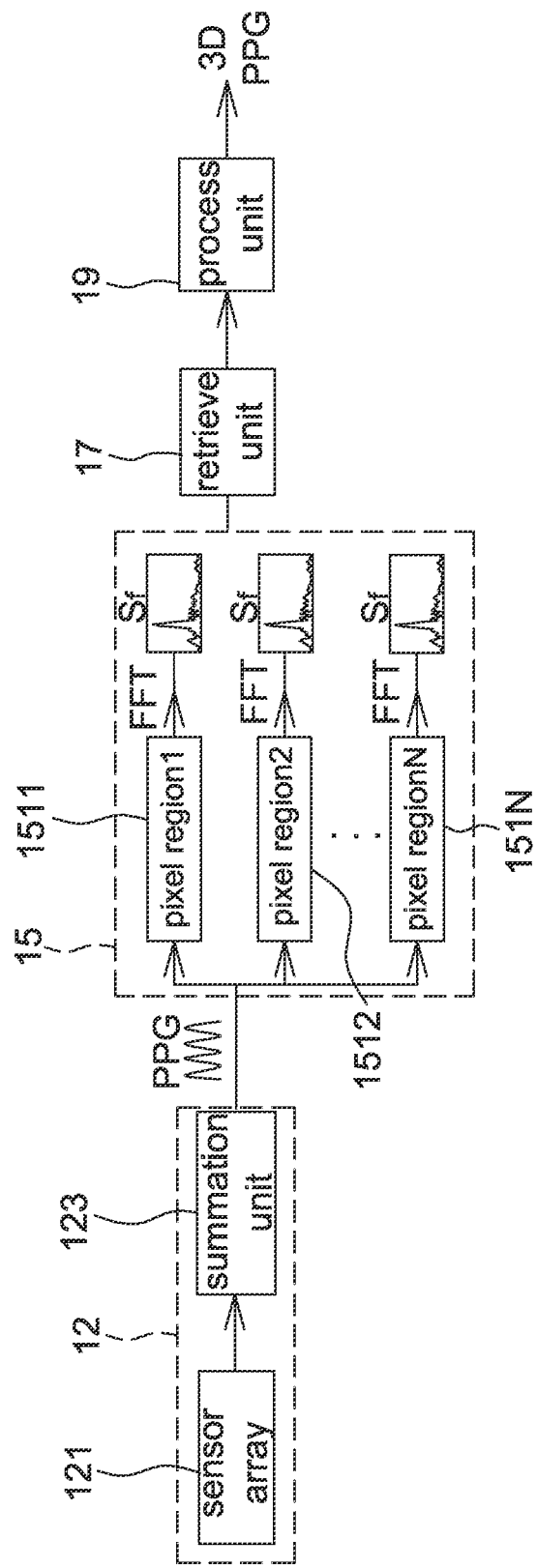
FIG. 2 is a schematic block diagram of an operating method of a physiological detection system according to one embodiment of the present disclosure.
Figure 3:
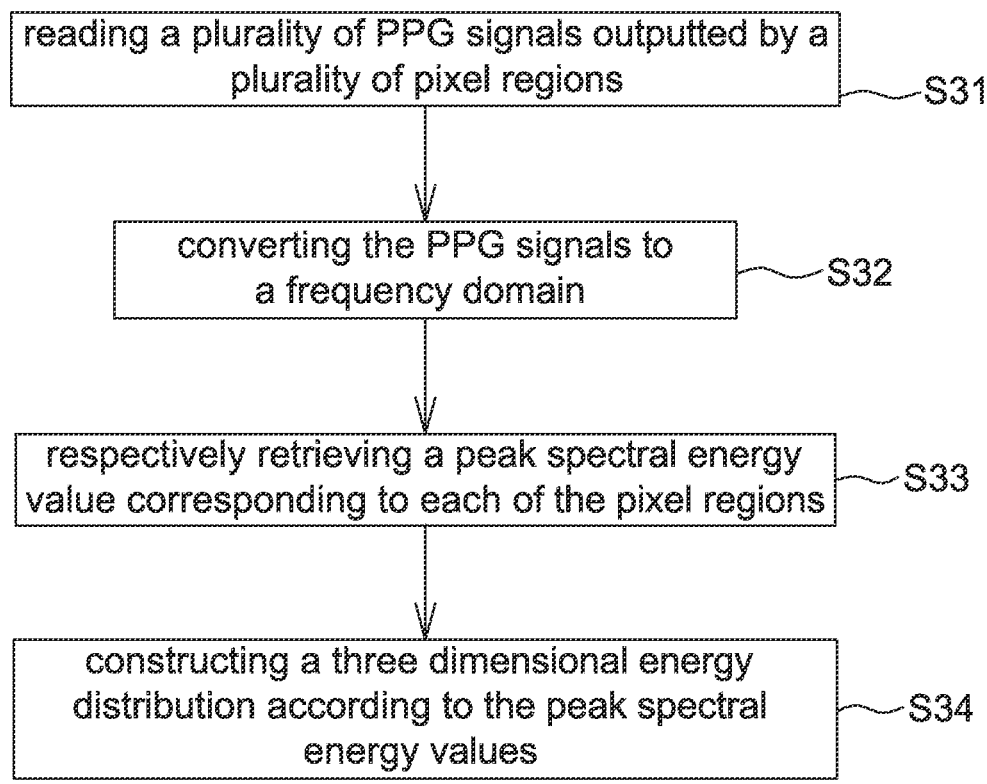
FIG. 3 is a flow chart of an operating method of the physiological detection system of FIG. 2.

Referring to FIGS. 2 and 3, FIG. 2 is a schematic block diagram of an operating method of a physiological detection system according to one embodiment of the present disclosure, and FIG. 3 is a flow chart of an operating method of the physiological detection system of FIG. 2. In this embodiment, the image sensor 12 is shown to include a sensor array 121 and a summation unit 123, wherein the summation unit 123 is configured to add the PPG signals of a plurality of pixels included in a plurality of pixel regions to output a sum of PPG signals. In other words, the image sensor 12 outputs a plurality of sum of PPG signals. As mentioned above, the summation unit 123 is implemented by hardware and/or software without particular limitations, e.g. included in a DSP of the image sensor 12. In addition, when a plurality of pixels of the image sensor 12 is not divided as a pixel region, the summation unit 132 is not implemented.

The operating method of this embodiment includes the steps of: reading a plurality of PPG signals outputted by a plurality of pixel regions (Step S31); converting the PPG signals to a frequency domain (Step S32); respectively retrieving a peak spectral energy value corresponding to each of the pixel regions (Step S33); and constructing a three dimensional energy distribution according to the peak spectral energy values (Step S34).

Step S31: The image sensor 12 successively captures images corresponding to the lighting of the light source 11, e.g. capturing images at a frame rate. The plurality of pixels of the sensor array 121 detects light passing through body tissues for a predetermined time to respectively output a PPG signal, wherein said predetermined time is determined according to, for example, the frame rate of the image sensor 12 and the data required by the converting unit 15 in calculation, e.g. 5-10 seconds, but not limited thereto. As mentioned above, the image sensor 12 outputs the PPG signal sensed by each pixel or outputs a plurality of sum of PPG signals calculated by the summation unit 123 according to different applications.

Step S32: The converting unit 15 is configured to read the PPG signals (or sum of PPG signals) and respectively calculates the fast Fourier transformation (FFT) of the sum of PPG signals of the pixel regions (e.g. pixel region 1 to pixel region N shown herein) to generate a plurality of frequency domain signals Sf (as shown in FIG. 2), wherein in the frequency domain signals Sf a peak spectral energy value appears at the heartbeat frequency. In one embodiment, the converting unit 15 calculates the FFT of 1024 points corresponding to each of the pixel regions 151I to 151N.

Step S33: The retrieving unit 17 receives the frequency domain signals Sf and respectively retrieves a peak spectral energy value (e.g. maximum energy) corresponding to each of the pixel regions 151I-151N.

Step S34: Finally, the processing unit 19 constructs a three dimensional energy distribution according to the peak spectral energy values, e.g. directly distributing the peak spectral energy values in a two dimensional space or distributing a shift or a ratio of the peak spectral energy values in a two dimensional space. In some embodiments, the processing unit 19 further constructs a three dimensional energy variation of the three dimensional energy distribution with time and stores the three dimensional energy variation.

In some embodiments, to prevent errors from the noise influence (e.g. the movement occurred between the skin surface and the image sensor 12), the processing unit 19 further calculates a plurality of heartbeat values (e.g. N heartbeat values) according to a plurality of peak spectral frequencies associated with the peak spectral energy values, and determines an output heartbeat according to a distribution peak of the heartbeat values. For example, if a counting of pixel regions obtaining 65-heartbeats has the highest number, 65 is considered as a correct heartbeat to be outputted.

In this embodiment, said three dimensional energy distribution or said three dimensional energy variation is outputted, for example, to a display device for displaying, or provided to other devices for corresponding processing according to different applications.

Figure 4:
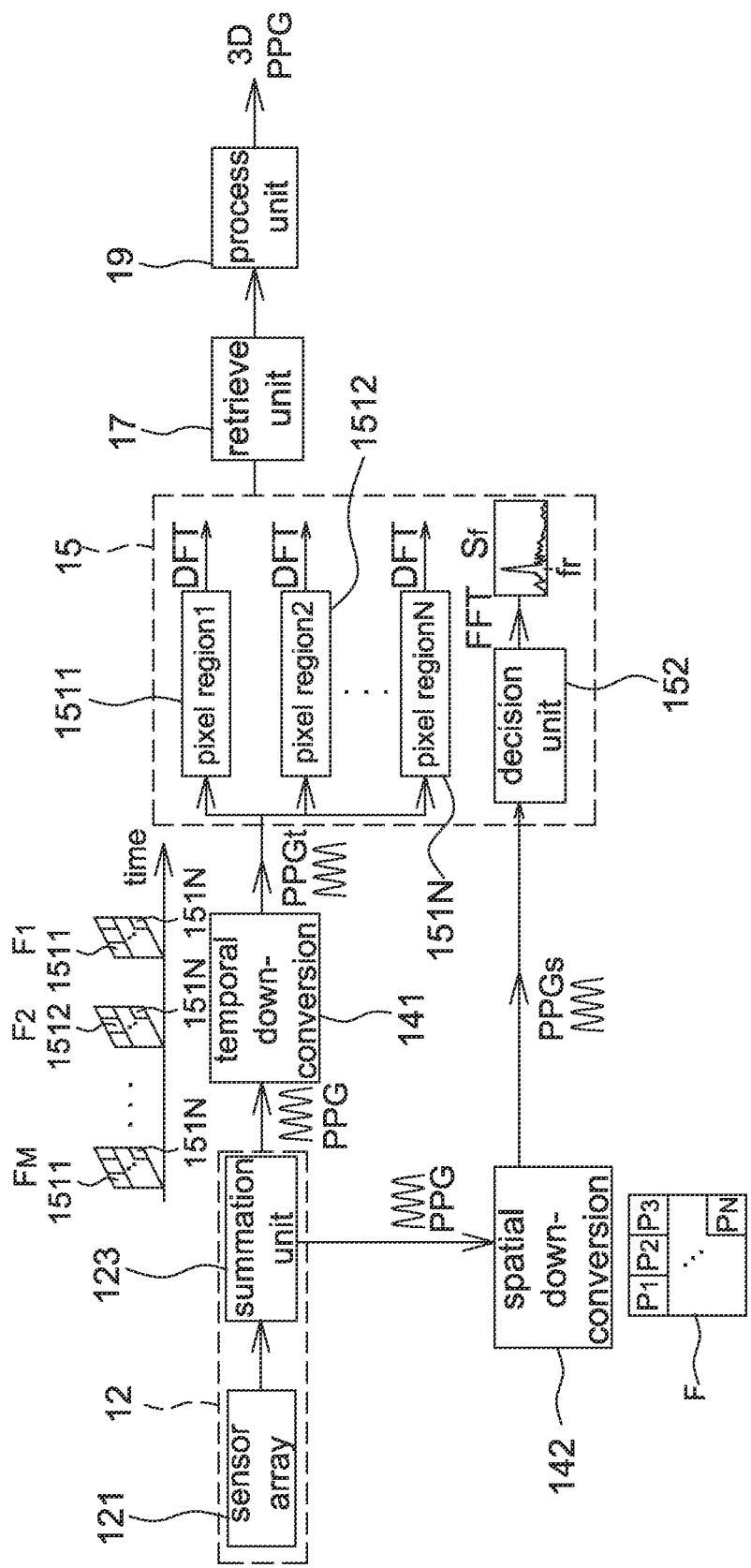
FIG. 4 is a schematic block diagram of an operating method of a physiological detection system according to another embodiment of the present disclosure.
Figure 5:
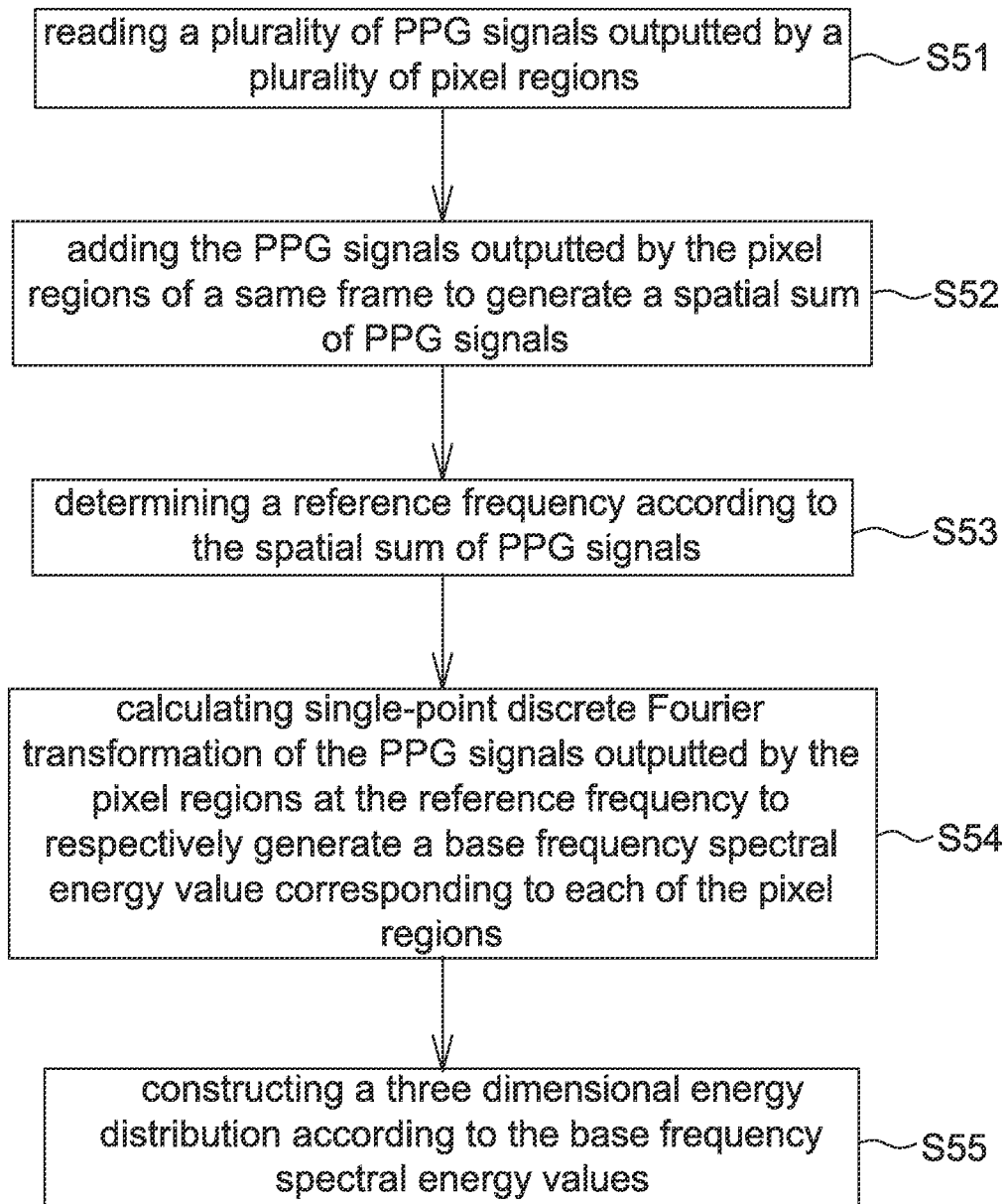
FIG. 5 is a flow chart of an operating method of the physiological detection system of FIG. 4.

Referring to FIGS. 4 and 5, FIG. 4 is a schematic block diagram of an operating method of a physiological detection system according to another embodiment of the present disclosure, and FIG. 5 is a flow chart of an operating method of the physiological detection system of FIG. 4. Compared with FIGS. 2-3, the operating method of this embodiment is suitable to reduce data amount calculated in the frequency conversion when the image sensor operates in a high frame rate (e.g. 3,000 frames/second). In this embodiment, the summation unit 123 is optionally implemented according to different embodiments.

The operating method includes the steps of: reading a plurality of PPG signals outputted by a plurality of pixel regions (Step S51); adding the PPG signals output by the pixel regions of a same frame to generate a spatial sum of PPG signals (Step S52); determining a reference frequency according to the spatial sum of PPG signals (Step S53); calculating single-point discrete Fourier transformation of the PPG signals outputted by the pixel regions at the reference frequency to respectively generate a base frequency spectral energy value corresponding to each of the pixel regions (Step S54); and constructing a three dimensional energy distribution according to the base frequency spectral energy values (Step S55).

Step S51: The image sensor 12 successively captures images corresponding to the lighting of the light source 11, e.g. capturing images at a frame rate. The plurality of pixels of the sensor array 121 detects the light passing through body tissues for a predetermined time to respectively output a PPG signal. As mentioned above, the image sensor 12 outputs the PPG signal sensed by each pixel or outputs a plurality of sum of PPG signals calculated by the summation unit 123 according to different applications.

Step S52: In this embodiment, the physiological detection system 1 further includes a spatial down-conversion unit 142 configured to add the PPG signals outputted by the pixel regions of a same frame so as to generate a spatial sum of PPG signals PPGs according to a plurality of frames captured within the predetermined time. For example, each frame F outputted by the image sensor 12 includes N pixel regions $P_1$~$P_N$. The spatial down-conversion unit 142 adds gray values of all pixel regions $P_1$~$P_N$ of each frame F (i.e. adding gray values of all pixels of each frame F).

Step S53: The converting unit 15 is configured to determine a reference frequency fr according to the spatial sum of PPG signals PPGs. In one embodiment, the converting unit 15 determines the reference frequency fr in time domain directly according to the spatial sum of PPG signals PPGs, e.g. calculating the reciprocal of a time interval between peak values (e.g. between maximum values or between minimum values) of the spatial sum of PPG signals PPGs. In another embodiment, the converting unit 15 firstly converts the spatial sum of PPG signals PPGs to a frequency domain and then determines the reference frequency fr according to a peak spectral frequency. For example, the converting unit 15 calculates fast Fourier transformation of the spatial sum of PPG signals of 1024 points and obtains a peak spectral frequency at the peak spectral energy value to be served as the reference frequency fr. For example, FIG. 4 shows that the converting unit 15 further includes a decision unit 152 configured to calculate a frequency domain signal Sf of the spatial sum of PPG signals PPGs and determines a peak spectral frequency thereof.

Step S54: The converting unit 15 then calculates single-point discrete Fourier transformation (DFT) of the PPG signals of the pixel regions at the reference frequency fr so as to respectively generate a base frequency spectral energy value corresponding to each of the pixel regions 1511-151N (i.e. N base frequency spectral energy values).

Step S55: Finally, the retrieving unit 17 retrieves the base frequency spectral energy values and then transmits the base frequency spectral energy values to the processing unit 19. The processing unit 19 then constructs a three dimensional energy distribution according to the base frequency spectral energy values, and further constructs a three dimensional energy variation of the three dimensional energy distribution with time for being stored.

In addition, the above two embodiments further include a temporal down-conversion unit 141 configured to add PPG signals of corresponding pixel regions in different frames (e.g. pixel region-by-pixel region) to respectively generate a temporal sum of PPG signals PPGt. For example, FIG. 4 shows frames $F_1$ to $F_M$. The temporal down-conversion unit 141 adds PPG signals of the pixel regions 1511 of a plurality of frames (e.g. 150 frames) to generate a temporal sum of PPG signals associated with the pixel region 1511, adds PPG signals of the pixel regions 1512 of a plurality of frames to generate a temporal sum of PPG signals associated with the pixel region 1512, . . . , and adds PPG signals of the pixel regions 151N of a plurality of frames to generate a temporal sum of PPG signals associated with the pixel region 151N (i.e. N temporal sum of PPG signals). The converting unit 15 then converts the temporal sum of PPG signals PPGt of the pixel regions 1511 to 151N to a frequency domain. For example in the embodiment of FIG. 2, the converting unit 15 calculates fast Fourier transformation of the temporal sum of PPG signals PPGt of the pixel regions 1511 to 151N. For example in the embodiment of FIG. 4, the converting unit 15 calculates single-point discrete Fourier transformation of the temporal sum of PPG signals PPGt of the pixel regions 1511 to 151N at the base frequency fr. In this way, it is able to effectively reduce the data amount calculated by the converting unit 15. It should be mentioned that if FIG. 2 further includes a temporal down-conversion unit, the temporal down-conversion unit is electrically coupled to the image sensor 12.

In some embodiments, it is possible to reduce the data amount processed by the converting unit 15 according to a variation tendency of the predicted physiological value. For example, when the converting unit 15 converts the PPG signals to a frequency domain, it is able to predict a range in which the peak frequency will fall into later according to a previous variation tendency of the peak spectral frequencies so as to select a number of points used in performing the fast Fourier transformation, e.g. reduced from 1024 points to 256 points, so as to increase the reaction speed and reduce the data amount to be processed.

In some embodiments, the physiological detection system 1 further performs an auto exposure function according to the detection signal outputted by the image sensor 12, e.g. an average value of the PPG signals of one frame, so as to increase the detection accuracy. For example, when the average value is lower than a first threshold, the exposure time, light intensity and/or diaphragm is increased; whereas when the average value is higher than a second threshold, the exposure time, light intensity and/or diaphragm is decreased.

It should be mentioned that values given in the above embodiments, e.g. the pixel number, pixel region number, points used in FFT, frame rate and so on, are only intended to illustrate but not to limit the present disclosure. The actual values are determined according to different applications without particular limitations.

As mentioned above, the physiological detection function is gradually applied to various portable electronic devices and wearable electronic devices nowadays. Therefore, the present disclosure provides a physiological detection system (FIG. 1) and an operating method thereof (FIGS. 2-5) that construct a three dimensional energy distribution according to a plurality of photoplethysmographic (PPG) signals outputted by a plurality of pixel regions and record a three dimensional energy variation of the three dimensional energy distribution with time so as to realize a portable 3D physiological monitoring device.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A host, configured to receive a plurality of PPG signals each corresponding to one pixel region of a frame acquired by a wearable device, the host comprising:
    a converting unit configured to convert each of the PPG signals to a frequency domain signal thereby generating a plurality of frequency domain signals each corresponding to one of the pixel regions of the frame;
    a retrieving unit configured to respectively retrieve a spectral energy value of the frequency domain signals corresponding to each of the pixel regions;
    a processing unit configured to construct a three dimensional energy distribution of spectral energy values, each spectral energy value corresponding to one of the pixel regions, by distributing the spectral energy values in a two dimensional space corresponding to the pixel regions as the three dimensional energy distribution that has an energy value corresponding to each of the pixel regions; and
    a display configured to display the three dimensional energy distribution.

2. The host as claimed in claim 1, wherein the processing unit is further configured to construct a three dimensional energy variation of the three dimensional energy distribution with time.

3. The host as claimed in claim 1, wherein
    each of the pixel regions comprises a plurality of pixels of the frame, and
    each of the received PPG signals is a sum of PPG signals of the plurality of pixels in each of the pixel regions.

4. The host as claimed in claim 3, wherein said sum of PPG signals is a sum of analog PPG signals or a sum of digital PPG signals.

5. The host as claimed in claim 1, further configured to receive
a spatial sum of PPG signals generated by adding the plurality of PPG signals corresponding to the pixel regions in a same frame.

6. The host as claimed in claim 5, wherein the converting unit is configured to
determine a reference frequency according to the spatial sum of PPG signals, and
calculate single-point discrete Fourier transformation of the received PPG signals corresponding to the pixel regions at the reference frequency so as to respectively generate a base frequency spectral energy value corresponding to each of the pixel regions.

7. The host as claimed in claim 6, wherein
the received PPG signals is a plurality of temporal sum of PPG signals respectively generated by adding PPG signals of corresponding pixel regions of different frames.

8. The host as claimed in claim 7, wherein the converting unit is configured to calculate single-point discrete Fourier transformation of the received PPG signals corresponding to the pixel regions at the reference frequency.

9. The host as claimed in claim 1, wherein the host is configured to receive the plurality of PPG signals wired or wirelessly.

10. The host as claimed in claim 1, wherein each of the pixel regions comprises at least one pixel of the frame.

11. A physiological detection system, comprising:
a wearable device configured to output a plurality of PPG signals each corresponding to one pixel region of a frame acquired thereby; and
a host, configured to receive the plurality of PPG signals from the wearable device, and comprising:
a converting unit configured to convert each of the PPG signals to a frequency domain signal thereby generating a plurality of frequency domain signals each corresponding to one of the pixel regions of the frame;
a retrieving unit configured to respectively retrieve a spectral energy value of the frequency domain signals corresponding to each of the pixel regions;
a processing unit configured to construct a three dimensional energy distribution of spectral energy values, each spectral energy value corresponding to one of the pixel regions, by distributing the spectral energy values in a two dimensional space corresponding to the pixel regions as the three dimensional energy distribution that has an energy value corresponding to each of the pixel regions; and
a display configured to display the three dimensional energy distribution.

12. The physiological detection system as claimed in claim 11, wherein the processing unit is further configured to construct a three dimensional energy variation of the three dimensional energy distribution with time.

13. The physiological detection system as claimed in claim 11, wherein
each of the pixel regions comprises a plurality of pixels of the frame, and
each of the plurality of PPG signals is a sum of PPG signals of the plurality of pixels in each of the pixel regions.

14. The physiological detection system as claimed in claim 13, wherein said sum of PPG signals is a sum of analog PPG signals or a sum of digital PPG signals.

15. The physiological detection system as claimed in claim 11, wherein the host is further configured to receive from the wearable device
a spatial sum of PPG signals generated by adding the plurality of PPG signals corresponding to the pixel regions in a same frame.

16. The physiological detection system as claimed in claim 15, wherein the converting unit is configured to
determine a reference frequency according to the spatial sum of PPG signals, and
calculate single-point discrete Fourier transformation of the plurality of PPG signals corresponding to the pixel regions at the reference frequency so as to respectively generate a base frequency spectral energy value corresponding to each of the pixel regions.

17. The physiological detection system as claimed in claim 16, wherein
the plurality of PPG signals is a plurality of temporal sum of PPG signals respectively generated by adding PPG signals of corresponding pixel regions of different frames.

18. The physiological detection system as claimed in claim 17, wherein the converting unit is configured to calculate single-point discrete Fourier transformation of the plurality of PPG signals corresponding to the pixel regions at the reference frequency.

19. The physiological detection system as claimed in claim 11, wherein the host is configured to receive the plurality of PPG signals wired or wirelessly.

20. The physiological detection system as claimed in claim 11, wherein each of the pixel regions comprises at least one pixel of the frame.

* * * * *